US010436680B2

(12) United States Patent
Peyvan

(10) Patent No.: US 10,436,680 B2
(45) Date of Patent: Oct. 8, 2019

(54) CAPTURE, DISRUPTION, AND EXTRACTION APPARATUS AND METHOD

(71) Applicant: Kianoosh Peyvan, Seattle, WA (US)

(72) Inventor: Kianoosh Peyvan, Seattle, WA (US)

( * ) Notice: Subject to any disclaimer, the term of this patent is extended or adjusted under 35 U.S.C. 154(b) by 821 days.

(21) Appl. No.: 14/512,428

(22) Filed: Oct. 11, 2014

(65) Prior Publication Data

US 2015/0104825 A1  Apr. 16, 2015

Related U.S. Application Data

(60) Provisional application No. 61/891,043, filed on Oct. 15, 2013.

(51) Int. Cl.
*G01N 1/28* (2006.01)

(52) U.S. Cl.
CPC ..... *G01N 1/286* (2013.01); *G01N 2001/2866* (2013.01)

(58) Field of Classification Search
CPC ............ G01N 1/286; G01N 2001/2866; B02C 17/10; B02C 17/20; C12M 45/02; C12M 47/06; C12M 1/33; C12M 1/00
See application file for complete search history.

(56) References Cited

U.S. PATENT DOCUMENTS

| | | |
|---|---|---|
| 4,495,282 A | 1/1985 | Ohnishi et al. |
| 4,745,074 A | 5/1988 | Schreier et al. |
| 5,702,884 A | 12/1997 | Ekeze et al. |
| 6,287,831 B1 | 9/2001 | Tai et al. |
| 6,534,295 B2 | 3/2003 | Tai et al. |
| 6,664,049 B1 | 12/2003 | Chevalier |
| 6,673,556 B2 | 1/2004 | Nixon et al. |
| 6,699,706 B1 | 3/2004 | Brooks |
| 6,815,209 B2 | 11/2004 | Baeummer et al. |
| 6,942,169 B2 | 9/2005 | Sparks |
| 7,176,018 B2 | 2/2007 | Tai et al. |
| 7,186,516 B2 | 3/2007 | Nixon et al. |
| 7,319,021 B2 | 1/2008 | Engel et al. |
| 7,488,596 B2 | 2/2009 | Lee et al. |
| 7,517,690 B2 | 4/2009 | Han et al. |

(Continued)

*Primary Examiner* — William H. Beisner
*Assistant Examiner* — Danielle B Henkel
(74) *Attorney, Agent, or Firm* — Nima Seyedali

(57) ABSTRACT

A cell capture, disruption, and extraction apparatus includes a disruption chamber configured to receive cell solution and having therein a plurality of abrasives, which can include diamond powder, variably and multi dimensionally disbursed therein, and a pestle positioned in the disruption chamber. The apparatus includes an actuation device configured to agitate the disruption chamber and/or pestle, movement of the abrasives tearing cell structure in the solution to access its contents. A binding column or size exclusion column can be positioned downstream of the disruption chamber. The pestle can rotate with respect to the disruption chamber. The pestle can include a nut-shaped core or axle, and/or include a plurality of extrusions. Cell solution can first be introduced in the disruption chamber, the abrasives capturing the cells and allowing therethrough and purging the waste content, then breaking the cell content through the foregoing agitation process. The lysate can then bind to an extraction matrix downstream of the disruption chamber or it can be mixed in with the abrasives.

13 Claims, 12 Drawing Sheets

(56) References Cited

U.S. PATENT DOCUMENTS

| | | |
|---|---|---|
| 7,521,246 B2 | 4/2009 | Yang et al. |
| 7,534,772 B2 | 5/2009 | Weiner et al. |
| 7,598,064 B2 | 10/2009 | Lee et al. |
| 8,357,672 B2 | 1/2013 | Diges et al. |
| 8,404,440 B2 | 3/2013 | Solli et al. |
| 8,637,285 B2 | 1/2014 | Ussing |
| 8,986,986 B2 | 3/2015 | Hwang et al. |
| 9,073,053 B2 | 7/2015 | Taylor et al. |
| 9,096,823 B1 | 8/2015 | Branch et al. |
| 2002/0019060 A1* | 2/2002 | Petersen ............... B01L 3/502 436/514 |
| 2008/0223962 A1* | 9/2008 | Kemppainen ........... B02C 17/10 241/2 |
| 2010/0159507 A1* | 6/2010 | Ting ...................... C12M 35/04 435/40.5 |
| 2010/0297754 A1 | 11/2010 | Solli et al. |
| 2012/0256027 A1 | 10/2012 | Yang et al. |
| 2014/0231256 A1 | 8/2014 | Packingham et al. |
| 2014/0234890 A1 | 8/2014 | Gjerde |
| 2014/0322697 A1 | 10/2014 | Wong et al. |
| 2014/0342348 A1 | 11/2014 | Lee et al. |
| 2014/0363822 A1 | 12/2014 | Chiesl |
| 2015/0184127 A1 | 7/2015 | White et al. |

\* cited by examiner

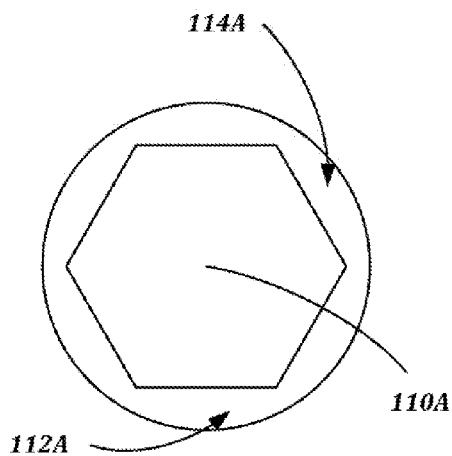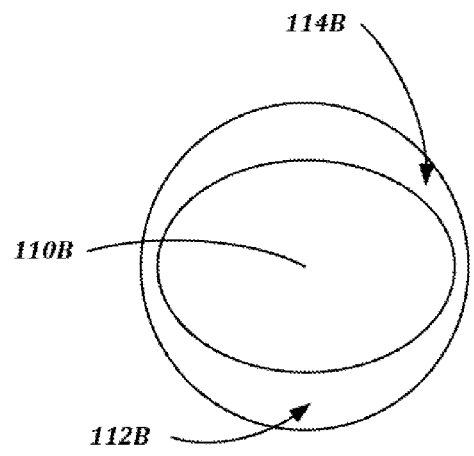
FIG.2A    FIG.2B
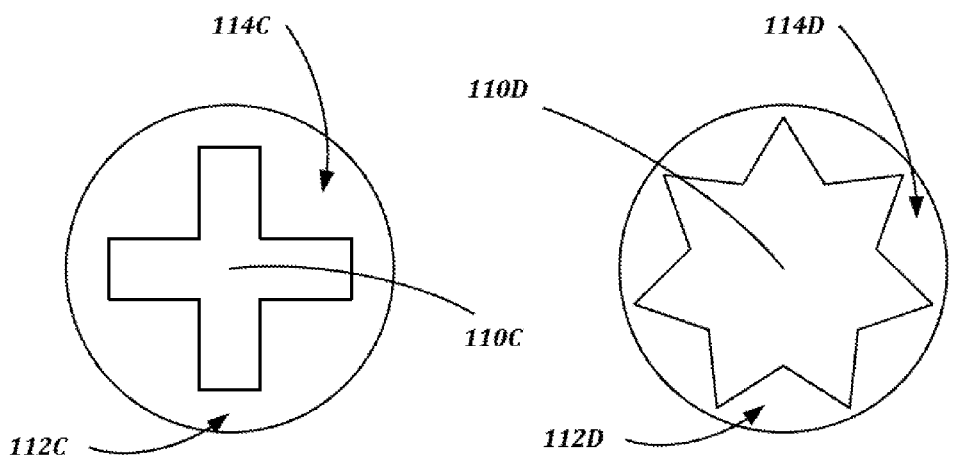
FIG.2C    FIG.2D

US 10,436,680 B2

CAPTURE, DISRUPTION, AND EXTRACTION APPARATUS AND METHOD

STATEMENT REGARDING GOVERNMENT LICENSE RIGHTS

A portion of the disclosure herein was made with Government support under Contract No. NNA09DA96C by The National Aeronautics and Space Administration. The government has certain rights in the disclosure.

BACKGROUND

Technical Field

The present disclosure generally relates to cell capture, disruption, and extraction, and more particularly, to a device and method for receiving, isolating, and preparing cell lysate and extraction of specific cell content such as nucleic acid, proteins, lipid and the like.

Description of the Related Art

Typical starting materials for genomics or proteomics assays are biological samples. These samples could include, among others, plant or animal tissue, cultured bacteria, yeast, algae, blood and/or other bodily fluids. To extract any part of the cellular components from these samples, the cells are typically removed from media in which they exist, such as growth or storage solution, or otherwise concentrated into a small volume. The cell membrane and/or cell walls are then broken to expose its content (lysis). Some cells may have a thin membrane that can be broken by simply exposing them to chaotropic salts such as guanidinium thiocyanate. Other cells, such as plant and single cell blue green algae, have thicker cell membranes or additional cell walls, making them difficult to break. Bacteria spores such as *bacillus, subtilis* or *anthracis* form strong bacteria spores, which are also difficult to break.

Furthermore, typically a targeted material, which can be DNA, RNA, Protein, lipids, or other cellular material, is extracted through methods such as affinity columns from prepared cell lysate.

Existing methods to perform the steps above are carried out using distinct individual tools and kits performing these steps separately, and their technologies for performing these steps do not lend to performing combination-processing steps. For example, filter membranes are used to separate the cells from its surrounding media. Harsh chemical, heat, Sonication, Freeze/Thaw and/or bead beating are used to break cells open.

Commercially available filters currently used for cell separation or concentration purposes, are slow and eventually clog. Furthermore, existing devices typically collect cells from the filter, then remove it and move it to a separate lysis tube. This transport can be prone to handling errors and contamination, is labor intensive, and reduces overall lysis yield and quality.

Therefore, existing devices consume excess time and expense to perform complete sample preparation and target material extraction, and are prone to contamination and/or destruction of intracellular components being sought. Furthermore, existing methods may not be reproducible; may be applicable to only one of small scale or large scale processing; can exhibit high noise levels, yield variability, and generation of free radicals; can only be applicable to easily breakable cells; may not work with microorganisms; are slow and susceptible to clogging; and/or require expensive, complicated, super high speed breakup mechanism, and/or be prone to contaminating external elements.

BRIEF SUMMARY

According to one embodiment, a cell capture, disruption, and extraction apparatus includes a disruption chamber having an inlet and an outlet, a pestle at least a portion of which is configured to be received in the disruption chamber, a plurality of abrasive particles positioned in the disruption chamber, and an actuating mechanism operatively coupled to at least one of the disruption chamber and the pestle, and configured to agitate at least one of the pestle and the disruption chamber.

In one aspect, the abrasives can be coarser toward the inlet and outlet of the disruption chamber, and more concentrated toward a middle region between the inlet and outlet.

In one aspect, the abrasives can be coarser toward the outlet of the disruption chamber, and more concentrated toward the inlet.

In one aspect, the apparatus includes an outlet port in fluid communication with the disruption chamber, and configured to communicate fluid from the disruption chamber to an environment outside of the apparatus.

In one aspect, the apparatus includes a binding matrix or column positioned between the disruption chamber outlet and the outlet port.

In one aspect, the apparatus includes an auxiliary port in fluid communication with the disruption chamber.

In one aspect, the abrasive particles include at least one of diamond, glass shreds, aluminum oxide, silicon dioxide, and glass fiber.

In one aspect, the apparatus includes a first mesh component positioned toward a first end of the disruption chamber, and a second mesh component positioned toward a second end of the disruption chamber, opposing the first end, the first and second mesh components retaining the abrasives.

According to one embodiment, an apparatus adapted to retain, filter, grind, and break cells includes a first fitting forming therein a disruption chamber, a second fitting coupled to the first fitting and forming an outlet portion therein in fluid communication with the disruption chamber, an inlet port in fluid communication with the disruption chamber, a plurality of abrasives positioned in the disruption chamber forming a multi-dimensional filtration and grinding tool, the plurality of abrasives including at least first, second, and third layers, an actuation device operatively coupled to a pestle engaging the disruption chamber and configured to rotate therewith, and at least one retaining member including a mesh component, the at least one retaining member positioned adjacent at least one of the inlet and outlet of the disruption chamber.

In one aspect, the second layer of is denser than the first and third layers, and positioned therebetween.

According to one embodiment, a cell disruption chamber includes a disruption volume having an inlet and an outlet and configured to receive a cell sample containing cells, a plurality of abrasive particles positioned in the disruption chamber and configured to capture cells from cell solution and allow therethrough waste matter from cell solution, an inlet in fluid communication with the disruption chamber, and an outlet in fluid communication with the disruption volume.

In one aspect, the disruption chamber includes an actuating mechanism operatively coupled to the disruption chamber and configured to agitate the disruption chamber wherein the actuating mechanism includes a pestle configured to move, agitate, rotate, and/or shake the disruption chamber, grinding the abrasives against the cells.

In one aspect, the actuating mechanism further includes a manual or automatic actuator configured to effect relative motion between the pestle with respect to the disruption chamber volume.

In one aspect, the pestle includes a body coupled to or forming a plurality of extrusions configured to be positioned in the disruption chamber.

According to one embodiment, a method for isolating cells from cell solution includes introducing cell solution including cells and waste matter, into a disruption chamber including abrasives therein, capturing the cells against the abrasives and passing through the abrasives the waste content, communicating the waste content away from the disruption chamber, and agitating the cells against the abrasives, breaking open the cells and forming a lysate.

In one aspect, the method further includes communicating the lysate through a binding matrix.

In one aspect, the abrasives can be selected from a material such as silicon dioxide which can act as at least one of a filter, a lyser, and an extraction media.

According to one embodiment, a method of isolating and breaking cells from a cell solution includes using abrasive particles to capture cells, and agitating the abrasive particles to break open the cells.

In one aspect, the step of using abrasive particles to capture cells includes using diamond particles to capture cells.

In one aspect, the step of agitating the abrasive particles includes shaking the abrasive particles and rubbing the cells against the abrasive particles to break them open, forming a lysate.

FIGURE BRIEF DESCRIPTION OF THE SEVERAL VIEWS OF THE DRAWINGS

FIGS. 2A through 2D are each a cross-sectional view of the apparatus of FIG. 1, taken across section 2A, 2B, 2C, 2D, according to various embodiments.

DETAILED DESCRIPTION

Figure 1:
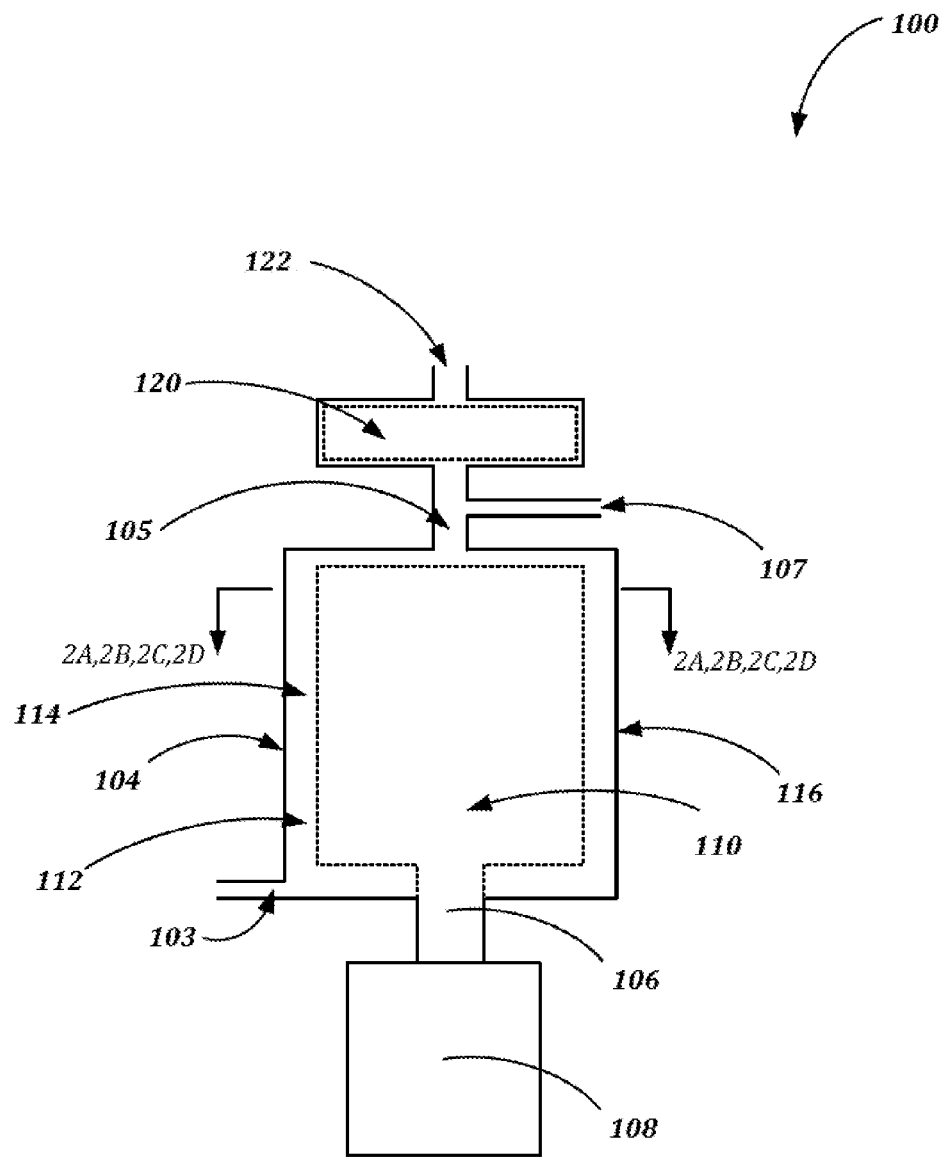
FIG. 1 is a side schematic view of a capture, disruption, and extraction apparatus according to one embodiment.

In one embodiment as illustrated in FIG. 1, a capture, disruption and extraction apparatus 100 includes a solution inlet port 103 and a cell disruption chamber 104 in fluid communication with the inlet port 103. In the illustrated embodiment of FIG. 1, the inlet port 103 is in direct fluid communication with the cell disruption chamber 104; however, in other embodiments, the inlet port 103 can be indirectly in fluid communication with the cell disruption chamber 104. In one aspect, instead of, or in addition to the inlet port 103, the apparatus 100 can include an auxiliary inlet/outlet port 107 formed a portion of the apparatus 100, which in turn is coupled directly or indirectly to the cell disruption chamber 104.

For example, according to one aspect, the auxiliary port 107 can be in fluid communication with the outlet port 105 where cell solution or abrasive content similar to that described above can first be introduced in the disruption chamber 104 prior to operation of the apparatus 100 to filter cell solution and sequentially exit the waste and filtered content out through outlet port 105. In some embodiments, the apparatus can be unassembled to introduce abrasives as later described.

In some aspects, the auxiliary port 107 can communicate waste or filtrate out of the apparatus 100 or away from the chamber 104 and outlet port 105, and/or allow abrasives and/or solution toward the chamber 104. Other embodiments may use the auxiliary port 107 to introduce wash fluid to a downstream location as will be described with respect to a binding matrix below.

In one aspect, the apparatus 100 can include an actuation device 108, which in some embodiments can be manual and/or automatic. For example, in some aspects, the actuation device 108 can include a motor. For clarity of description and without any intention to limit the scope of the present disclosure or the actuation device, the actuation device 108 will hereinafter be referred to as the motor 108.

The motor 108 can be operatively coupled with respect to the cell disruption chamber 104, for example via a shaft and/or a pestle, and/or a combination thereof, or any other suitable coupling member, to rotate, oscillate, move, or otherwise shake or agitate contents in the disruption chamber 104. In one aspect, the motor 108 can include or be coupled to a pestle 110 at least partially extending in the disruption chamber 104 as illustrated in FIGS. 1 and 2A through 2D, and configured to be rotated or moved therein, or effect rotation or movement of the disruption chamber 104. In one embodiment, for example, the motor 108 can be operatively coupled to the pestle 110 via an intermediate member 106 that can include or be a shaft, gear mechanism, screw or ball screw mechanism, any combination thereof, or any other suitable drive or rotation mechanism, system, or structure.

In one embodiment, a portion of the pestle 110 adapted to be received in the disruption chamber 104 can include a key member, a geometric shape, and/or a frictional feature or attribute, complementary to that formed in, coupled to, or attached to or on an outer surface thereof. In some embodiments, the pestle 110 can include an auger.

According to one aspect, the disruption chamber 104 includes a cavity 112 configured to receive the pestle 110, and a volume 114 between the pestle 110 and an outer wall 116 of the disruption chamber 104. In an aspect the volume 114 is adapted to receive fluid, liquid, solids, particles and/or any combination thereof, for example, a cell solution and/or abrasives as will be discussed with respect to certain embodiments below. In various embodiments, the pestle 110 can include a different shape and/or periphery to promote disruption and/or agitation in the volume 114.

For example, in the illustrated embodiment of FIG. 2A, a pestle 110A has a hexagonal outer surface configured to be received in a cavity 112A to form a volume 114A about the periphery of the outer surface of the pestle 110A. In other embodiments, the pestle 110 may include a different shape. For example, as illustrated in FIGS. 2B through 2D, pestles 110B, 110C, 110D can include an elliptical, cross, or star shaped outer periphery, respectively, forming volumes 112B, 112C, 112D, respectively about the periphery of the respective pestles 110B, 110C, 110D.

Various embodiments may include various forms of actuation. For example, the motor shaft can be coupled to an end of the disruption chamber and/or the pestle in some embodiments. In yet other embodiments, the rotating portion of the motor can surround or circumscribe the disruption chamber and/or the pestle to rotate one with respect to the other, or two rotate them in opposite directions. These and other suitable actuation mechanisms are contemplated to be within the scope of the present disclosure. In some embodiments, the motor can be coupled to the disruption chamber to impart motion thereto and the pestle can be stationary while the disruption chamber rotates when actuated. In yet some embodiments, the pestle and the disruption chamber can be actuated to rotate in substantially opposite radial directions.

Figure 3A:
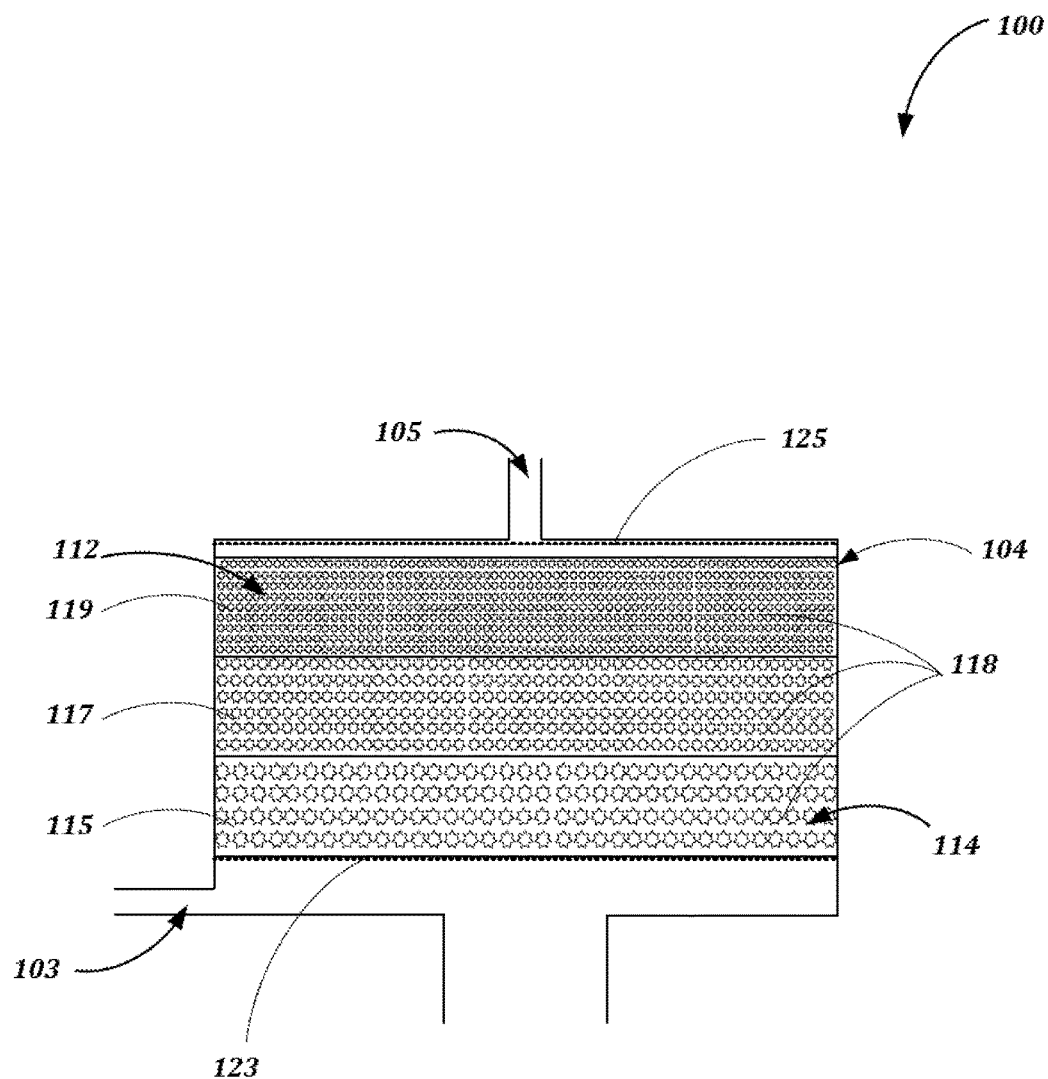
FIG. 3A is a side schematic view of a portion of the apparatus of FIG. 1 according to one embodiment.

FIG. 3A illustrates the volume 114 of an apparatus 100 according to one embodiment with the pestle 110 not shown for clarity of illustration. In one embodiment, the apparatus 100 includes an abrasive content 118 in the volume 114. In one aspect, in an application of the apparatus 100, cell solution is introduced via the inlet port 103, and fluidly communicated to the disruption chamber 104. In some embodiments, the disruption chamber 104 can be prefilled with the abrasive content 118. In an aspect, as the cell solution enters the disruption chamber 104, and negotiates its way through the abrasives 118, the abrasives 118 serve to guide and filter the solution, allowing through non-cell matter/fluid and isolating cells by trapping or obstructing them in the space formed between the abrasive particles.

In various embodiments, the abrasives 118 can be layered in multidimensional configuration, for example, a three dimensional configuration to facilitate guiding the cell solution in a first phase, and filtering it in a second phase or third phase. For example, the abrasives 118 can include a plurality of abrasive type, size or kind and/or a plurality of abrasive density and/or quantity. For example, in one embodiment, the volume 114 in cavity 112 may receive or house a group or layer of abrasives of a larger size 115, facilitating guiding the solution, adjacent a group or layer of abrasives of a medium size 117, which in turn is adjacent a group or layer of abrasives of a smaller size 119, which facilitates filtration/isolation of the cell from the cell solution. For better context, further below an example is provided as one embodiment for a thorough understanding of an embodiment of the present disclosure without any intent to limit the scope of the disclosure.

Some embodiments may include structure, components, and/or features to promote containment of the abrasives 118 in the chamber 104. For example, the apparatus 100 may include mesh and/or perforated layers or components 123, 125 positioned on opposing sides of the abrasives 118. For example, the mesh components 123, 125 can include a PEEK® mesh or other suitable fine mesh having a plurality of orifices or openings to contain the abrasives, such as 35 micron openings in some aspects.

In the description that follows and generally throughout this disclosure, nonlimiting examples of operation are described with respect to solutions being processed through various embodiments herein. Generally, separation of undesired solution content and desired solution content will be described. It is understood by those of skill in the art that the specifics of such content can vary. For example, the undesired content can include water, growth media, storage solution, waste matter, or any other content the user may desire to separate to isolate the desired content. The desired content can include cell content such as nucleic acid, proteins, lipid and the like. For clarity of description, the desired content will be referred to as cells or cell content and the undesired content will be referred to as waste matter, without any intention to limit the disclosure to any specific desired or undesired content.

In an aspect, solution such as cell solution is introduced to the chamber 104 through inlet port 103. In one aspect, the abrasives 118 obstruct, capture, and/or bind to desired fluid portions from the cell solution and substantially isolate the cells, while waste matter is purged through the outlet port 105 and/or the auxiliary port 107. In embodiment, when the waste matter is purged, the motor 108 actuate the pestle 110, initiating agitation and breaking up the cells from agitation through contact with and between the pestle 110, abrasives 118, and/or walls of the disruption chamber 104. In one embodiment, the abrasives 118 further serve to promote breaking open the cells as the motor 108 moves, rotates, oscillates, and/or otherwise agitates or shakes the pestle 110 and/or the cell disruption chamber 104, forcing the abrasives to shear, rub, or scrape against the cells, breaking them up and forming a desired broken cell slurry. Such cell slurry or lysate can then be fluidly communicated through the outlet port 105 via a wash step where fluid communicates the lysate away from chamber 104 toward a desired downstream destination.

In some embodiments, the abrasives can be selected from a group of materials that embody sharp edges, facilitating tearing cells even at slower speeds, thereby requiring less power, exhibiting less noise, more effectively breaking cells, even in micro applications, and operating at lesser speeds as compared to existing devices using purely shearing and/or bombarding or beating techniques. In some embodiments, the abrasives include diamond particle or diamond dust. In some embodiments, the abrasives can include, glass shreds, aluminum oxide, silicon dioxide or other suitable powder of appropriate size.

In some embodiments, the abrasive layers may be repeated in the same order to increase efficacy of the foregoing process. In some embodiments, the abrasive layers could include other combination of the layers. For example, the layers can progress from toward a first end of the chamber 104 to toward a second end of the chamber 104, opposing the first end, the abrasive layers can range sequentially in size and from large, to medium, to small, to medium, to large.

In some embodiments, the density or quantity of the abrasive or abrasives toward opposing terminal ends of the disruption chamber 104 can be greater than that toward the center of the chamber 104. In some embodiments, the variation in abrasive density and/or quantity from the opposing terminal ends of the disruption chamber 104 toward the center thereof can vary, and in one aspect, increase or decrease. For example, the abrasive content in the chamber 104 may include three abrasive layers from the terminal ends toward the center of the chamber 104. In such an aspect, the outer most layers closest to the terminal ends of the disruption chamber 104 can include abrasive of larger size distributed at a coarser spacing as compared to the same in the inner two layers toward the disruption chamber 104 central region.

Figure 3B:
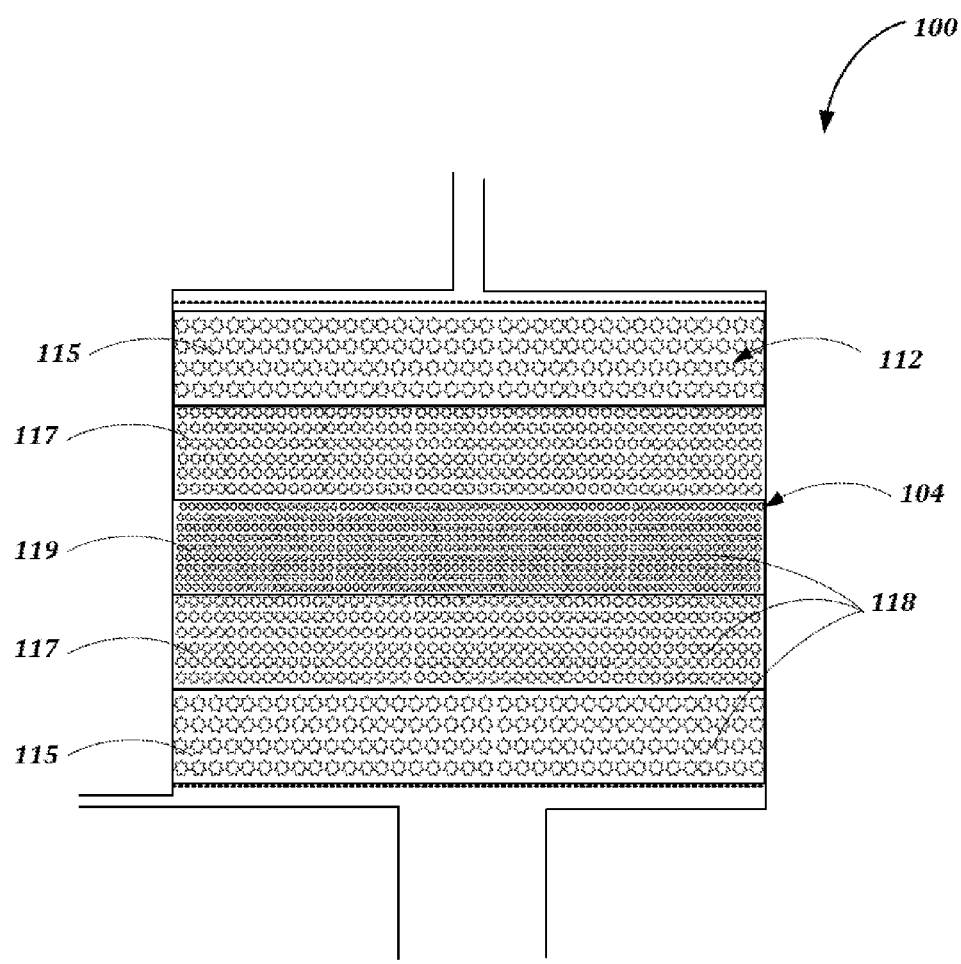
FIG. 3B is a side schematic view of a portion of the apparatus of FIG. 1 according to another embodiment.

For example, in one embodiment, as illustrated in FIG. 3B, the abrasives 118 in the chamber cavity 112 of chamber 104 can include outer layers of the abrasives of the larger size 115, intermediate layers of abrasives of the medium size 117 and a central layer of abrasives of the small size 119.

For better context, further below an example is provided as one embodiment for a thorough understanding of an embodiment of the present disclosure without any intent to limit the scope of the disclosure.

Therefore, embodiments of the present disclosure facilitate receiving, isolating, and breaking cells while mitigating the number and complexity of components used, and in an integrated process, to isolate cells and break them open exposing their content.

In some embodiments, as illustrated in FIG. 1, the apparatus 100 may include a solid phase extraction matrix, size exclusion matrix, or other suitable target specific capture matrix 120 configured to further isolate particular matter or material from the broken cells, such as RNA, DNA, protein, lipids or any combination thereof, and/or any other suitable matter or material desired to be extracted. In some embodiments, the matrix 120 can include a composite or other filtering material such as fiberglass, glass, sand, any combination thereof, and/or any other suitable frit, matrix, and/or binding or filtering material. In one aspect, the matrix 120 can include a Qiagen® RNA extraction membrane.

In some aspects, the extraction matrix 120 can be in fluid communication with the cell disruption chamber 104, for example with an outlet 105 thereof, the matrix 120 receiving the lysate following the above abrasive cell breaking process, further processing the lysate to extract a desired target, such as RNA, DNA, protein, lipids, any combination thereof, and/or any other suitable matter or material desired to be extracted. The auxiliary port 107 in one embodiment can also allow wash solution to be introduced to matrix 120, for example following the lysate having been communicated to the matrix 120.

In an aspect, as illustrated in FIG. 1, the apparatus 100 may further include a target outlet port or orifice 122 in fluid communication with the matrix 120 and adapted to receive the target matter or material and communicate it to an environment external to the apparatus 100 for use in a column, or in experiments and/or application in a subsequent chemical, biochemical, biotechnical, genomic and/or proteomic context.

Figure 4:
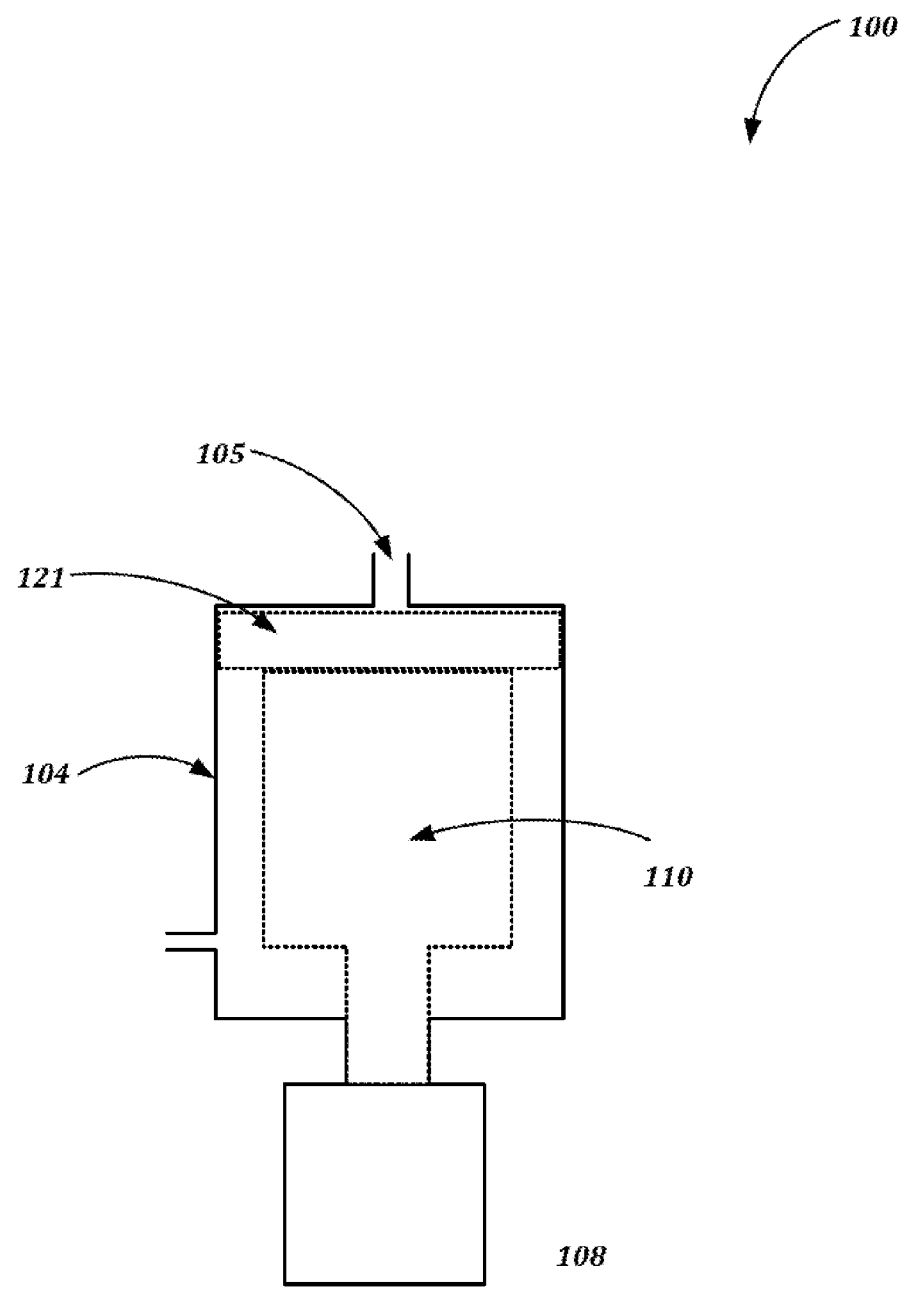
FIG. 4 is a side schematic view of a portion of the apparatus of FIG. 1 according to another embodiment.

In addition or instead, as illustrated in FIG. 4, in another aspect, the apparatus 100 may include an extraction matrix 121 between the outlet port 105 and the pestle 110.

Figure 5:
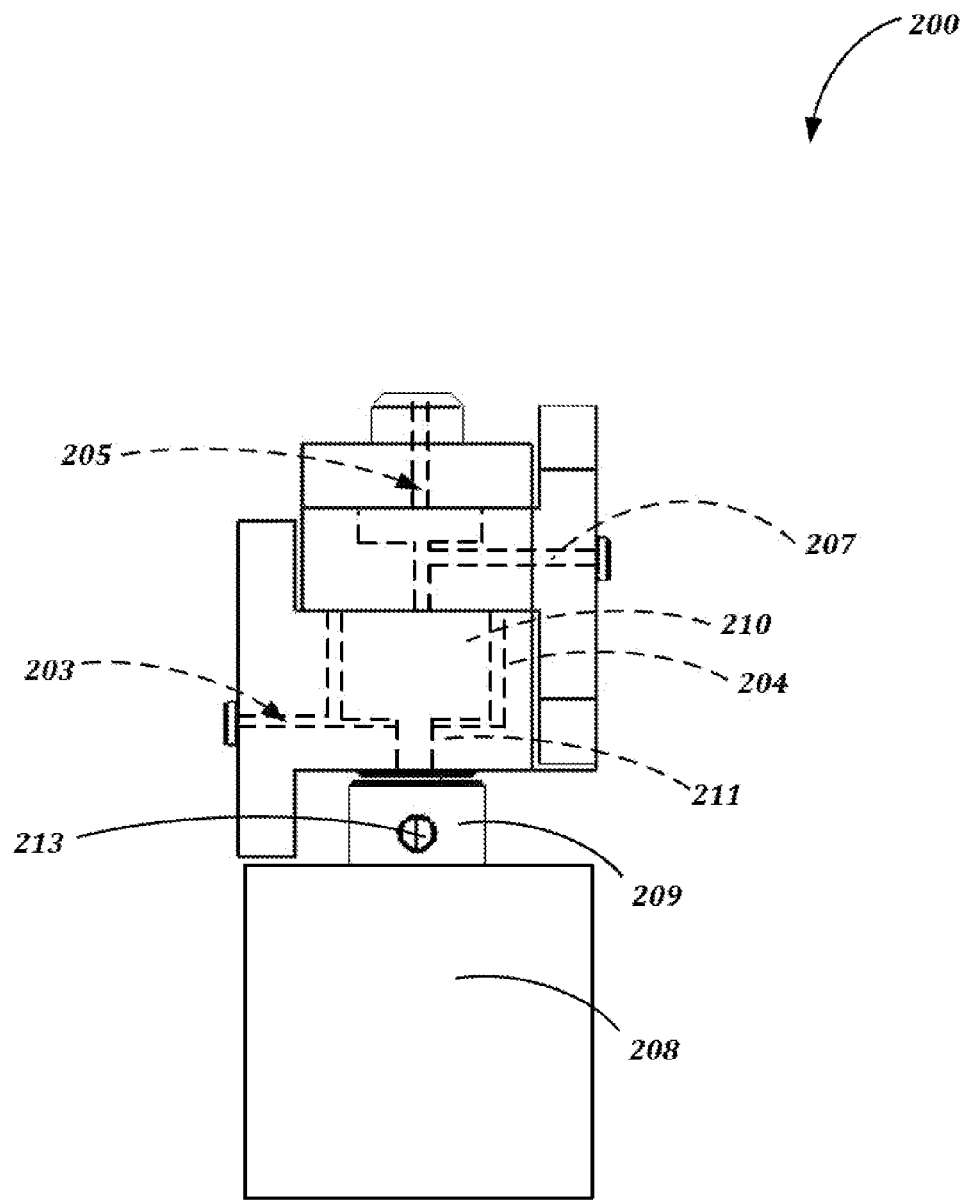
FIG. 5 is a side view of a capture, disruption, and extraction apparatus according to one embodiment.
Figure 6:
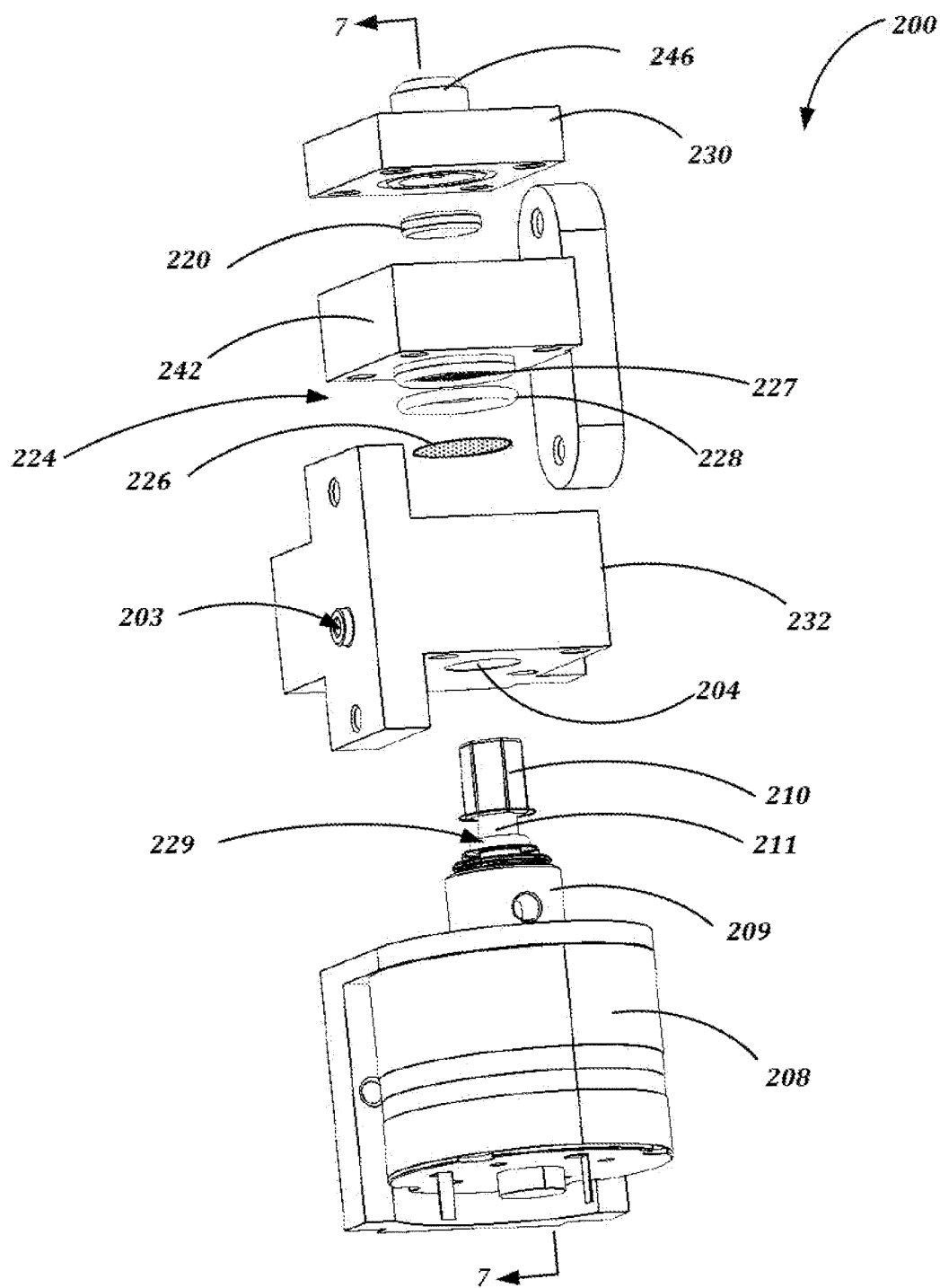
FIG. 6 is an exploded isometric view of the apparatus of FIG. 5 according to one embodiment.
Figure 7:
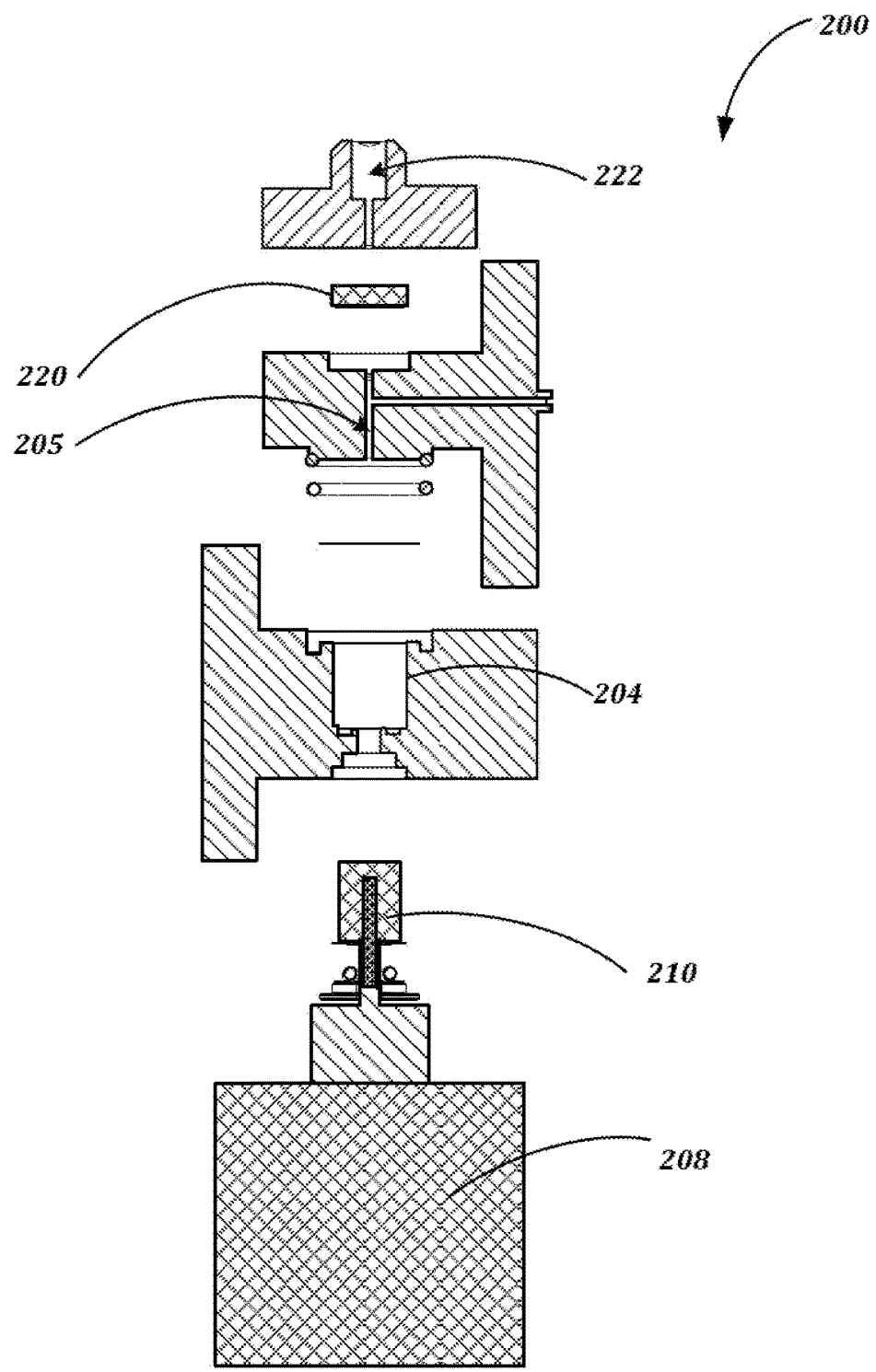
FIG. 7 is a cross-sectional view of the apparatus of FIG. 6, taken across section 7, according to one embodiment.

FIGS. 5, 6, and 7 illustrate an embodiment of a capture, disruption, and extraction apparatus 200 with some internal components shown in hidden lines. Not all internal components may have been shown in all these Figures for clarity of illustration. According to one embodiment, the apparatus 200 includes a solution inlet port 203, a cell disruption chamber 204 in fluid communication with the inlet port 203, and an outlet port 205 in fluid communication with the disruption chamber 204.

In one embodiment, the inlet port 203 is in direct fluid communication with the cell disruption chamber 204; however, in other embodiments, the inlet port 203 can be indirectly in fluid communication with the cell disruption chamber 204.

In one aspect, instead of, or in addition to the inlet port 203, the apparatus 200 can include an auxiliary inlet/outlet port 207 formed a portion of the apparatus 200, which in turn is coupled directly or indirectly to the cell disruption chamber 204.

For example, according to one aspect, the auxiliary port 207 can be in fluid communication with the outlet port 205 where cell solution or abrasive content similar to that described above can first be introduced in the disruption chamber 204 prior to operation of the apparatus 200 to filter cell solution and sequentially exit the waste and cells out through outlet port 205. In some aspects, the auxiliary port 207 can communicate waste or filtrate out of the apparatus 200 or away from the chamber 204 and outlet port 205, and/or allow abrasives and/or solution toward the chamber 204, or allow washing solutions to be introduce to matrix 220, for example following lysate and/or broken cell slurry having been communicated to the disruption chamber matrix 220 from chamber 104.

In one aspect, the apparatus 200 can include an actuation device 208, which in some embodiments can be manual and/or automatic. For example, in some aspects, the actuation device 208 can include a motor. For clarity of description and without any intention to limit the scope of the present disclosure or the actuation device, the actuation device 208 will hereinafter be referred to as the motor 208.

The motor 208 can be operatively coupled to at least one of the cell disruption chamber 204 or the pestle 210, for example via a shaft or any other suitable coupling member, to rotate, oscillate, move, or otherwise shake or agitate the disruption chamber 204. In one aspect, the motor 208 can include or be coupled to the pestle 210, which at least partially extends in the disruption chamber 204, and configured to be rotated or moved therewith, or effect rotation or movement of the pestle 210.

For example, the motor 208 can be coupled to the pestle 210 via a coupling member 209, which in one aspect can include a coupling shaft 211. In one aspect, the coupling member 209 can include a securing device 213 removably securing the shaft 211. For example, the securing device 213 can include a security screw, pin, or the like.

In one embodiment, a portion of the pestle 210 is adapted to be received in the disruption chamber 204. According to one aspect, the disruption chamber 204 includes a cavity 212 configured to receive the pestle 210, and a volume 214 between the pestle 210 and an outer wall 216 of the disruption chamber 204. In an aspect the volume 214 is adapted to receive abrasive layers and/or cell solution, for example, in one aspect, abrasive layers, followed by cell solution. In various embodiments, the pestle 210 can include a different shape and/or periphery to promote disruption and/or agitation of contents in the volume 214 as discussed above.

In one embodiment, in operation, cell solution can be introduced in the disruption chamber 204 via the inlet port 203 and/or the auxiliary inlet port 207, and disrupted through relative motion of the pestle 210 with respect to the disruption chamber 204.

In an aspect, abrasives can be introduced as discussed above in more detail to capture, obstruct, or trap cells and purge unwanted fluid portions or waste from the cell solution and substantially isolate the cells. In an aspect during or following purging of such waste matter, when the motor 208 actuates the pestle 210 and/or the disruption chamber 204, it induces breaking up the cells from agitation through contact with and between the pestle 210, abrasives 218, and/or walls of the disruption chamber 204. In one embodiment, the abrasives further serve to promote breaking open the cells as the motor 208 moves, rotates, oscillates, and/or otherwise agitates or shakes the pestle 210 and/or the cell disruption chamber 204, forcing the abrasives to shear, rub, or scrape against the cells, breaking them up and forming a desired broken cell slurry or lysate. Thereafter such slurry or lysate can be communicated and/or washed through the outlet port 105 to a desired destination for various desired applications.

In some embodiments, as illustrated in FIGS. 6 and 7, the apparatus 200 may include a solid phase extraction matrix, size exclusion matrix, or similar matrix 220 configured to further isolate particular matter or material from the broken cells, such as RNA, DNA, protein, lipids or any combination thereof, and/or any other suitable matter or material desired to be extracted. In some embodiments, the matrix 220 can include a composite or other filtering material such as fiberglass, glass, sand, any combination thereof, and/or any other suitable frit, matrix, and/or binding or filtering material. In one aspect, the matrix 220 can include a Qiagen® RNA extraction membrane.

In some aspects, the extraction matrix 220 can be in fluid communication with the cell disruption chamber 204, for example with an outlet 205 thereof, the matrix 220 receiving the lysate following the above abrasive cell breaking process, further processing the lysate to extract a desired target, such as RNA, DNA, protein, lipids, any combination thereof, and/or any other suitable matter or material desired to be extracted. In some embodiments, the material of which the matrix 220 is constructed such as silicon dioxide can be added in powder form and used in the chamber 204 in addition to, or instead of, the abrasives or be the abrasive.

In an aspect, the apparatus 200 may further include a target outlet port or orifice 222 in fluid communication with the matrix 220 and adapted to receive the target matter or material and communicate it to an environment external to the apparatus 200 for use in experiments and/or application in a subsequent chemical, biochemical, biotechnical, genomic and/or proteomic context.

In various embodiments, suitable structures and components can be used to house and/or form the foregoing features. For example, in one embodiment as illustrated in FIG. 6, the apparatus 200 includes a disruption fitting or housing 232 forming or containing the disruption chamber 204 and the inlet port 203; an outlet fitting 242 forming and/or housing the outlet port 205 and the auxiliary inlet/outlet 207; a clamping fitting 230; and an egress fitting 246. In some embodiments, the clamping fitting 230 and/or the egress fitting 246 where included, can form the target outlet port or orifice 222. In one embodiment, the housing 232, the motor 208, the outlet fitting 242, clamping fitting 230, and egress fitting 246, can be removably coupled to allow disassembling the apparatus 200.

As illustrated in FIG. 6, some embodiments may include a containment assembly 224 to contain the abrasives in the disruption chamber 204. In one aspect, the containment and filtering assembly 224 can include a mesh component 226 such as a PEEK® mesh or other suitable fine mesh having a plurality of orifices or openings to contain the abrasives.

In some embodiments, the containment assembly 224 may further include a filter positioned adjacent the mesh component 226, further fine filtering the disruption chamber contents. In some aspects, the apparatus 200 may include a seal or O-ring 228 adjacent the containment and filtering assembly 224, securing that assembly. In some embodiments, the apparatus 200 may include a seal or O-ring 229 between the pestle 210 and disruption chamber 204. In some embodiment the apparatus 200 includes a mesh element below the first layer of abrasives.

In some embodiments, the apparatus 200 includes the housing 232 in which the disruption chamber 204 is formed. In some aspects, the housing 232 further includes a gutter, depression, recess, or the like, configured to receive the containment and filtering assembly 224. In some aspects, the apparatus 200 can include the clamping fitting 230 configured to be coupled, fixedly or removably, to the housing 232, and having formed therein the outlet port 222, which can include a cavity, recess, channel, cylindrical opening, and/or any combination thereof, or other suitable port structure. In some aspects, the clamping fitting 230 may include grooves or channels 234 configured to promote or facilitate draining of fluid or cell slurry exiting the disruption chamber 204.

In some embodiments, the housing 232 may include a cavity, recess, channel, cylindrical opening, and/or any combination thereof, or other suitable port structure, forming the auxiliary inlet/outlet port 207 for introducing solution for being processed as disclosed herein. Alternative embodiments may include a distinct assembly or component coupled to the housing 232 to fluidly communicate therewith and introduce solution to the inlet 203 of the disruption chamber 204.

In one embodiment, the outlet fitting 242 and clamping fitting 230 can be removed to allow loading the chamber 204 with abrasives, then placing the containment assembly 224 to cover the chamber 204 and securing outlet fitting 242 and clamping fitting 230 to the disruption fitting 232 to prepare for introducing cell solution through inlet port 203.

In various embodiments, these features may be formed on either of the fittings or in some embodiments the fittings can be integrated and formed from a unitary body of material.

Various embodiments may include any suitable stabilizing, mounting, housing, and/or fluid feeding components for the apparatus 200. For example, the apparatus 200 can include an outer housing including first and second valve manifolds for communicating fluid in to and out of the disruption chamber 204.

Embodiments of the present disclosure therefore facilitate filtering and retaining cells and extracting their content in a simultaneous and/or sequential manner, thereby increasing efficiency and processing speeds while decreasing costs, labor, and chance of contamination. In addition, embodiments of the present disclosure can be used for additional processing such as washing samples with buffer solution and/or isolating active agent introducing contents exiting the disruption chamber to a binding matrix or frit.

The following example is provided for a thorough understanding of an embodiment having features according to some aspects, and makes reference to certain portions of the various embodiments and aspects discussed above; however, it is understood the present disclosure is not limited to what is described for this example and other embodiments are contemplated.

Other applications and combination of embodiments herein, for example, various abrasives, material, shapes, and actuation mechanisms, among other features, are contemplated to be within the scope of the present disclosure.

For example, in some embodiments, a cell capture, disruption, and extraction apparatus may include as its abrasive particles, silica, silicon dioxide, glass fiber or material similar or substantially identical to the solid phase extraction membrane/matrix, instead of, or in addition to, diamonds. In such an embodiment, a separate solid phase extraction matrix can be omitted, these particles performing disruption and extraction in the disruption chamber.

Furthermore, an apparatus according to various embodiments does not have to be limited to the specific combinations and features specifically described herein, and can be scaled or modifying without deviating from the scope of the present disclosure, to be suited for particular applications.

Figure 8:
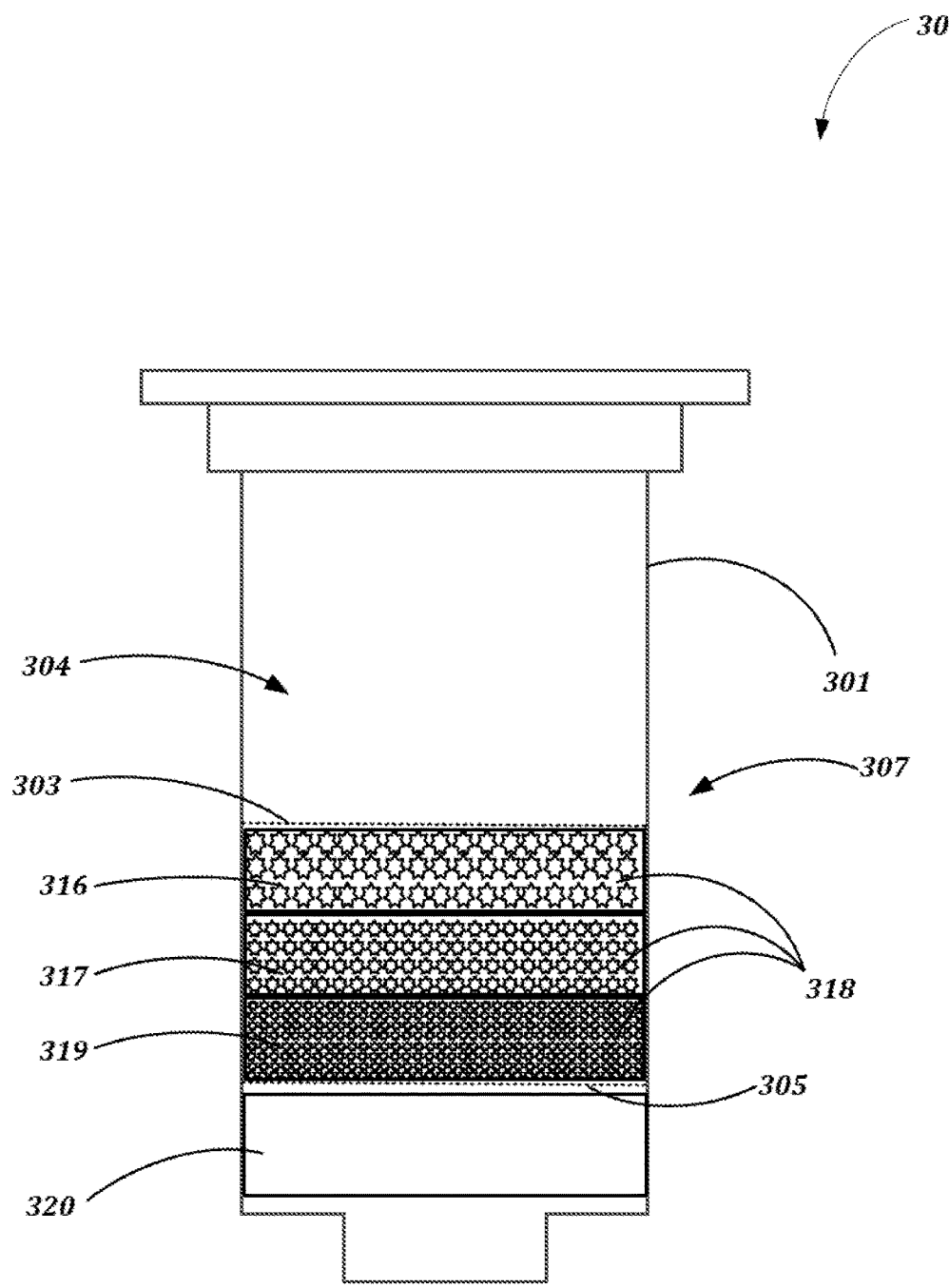
FIG. 8 is a portion of a capture, disruption, and extraction apparatus according to one embodiment.
Figure 9:
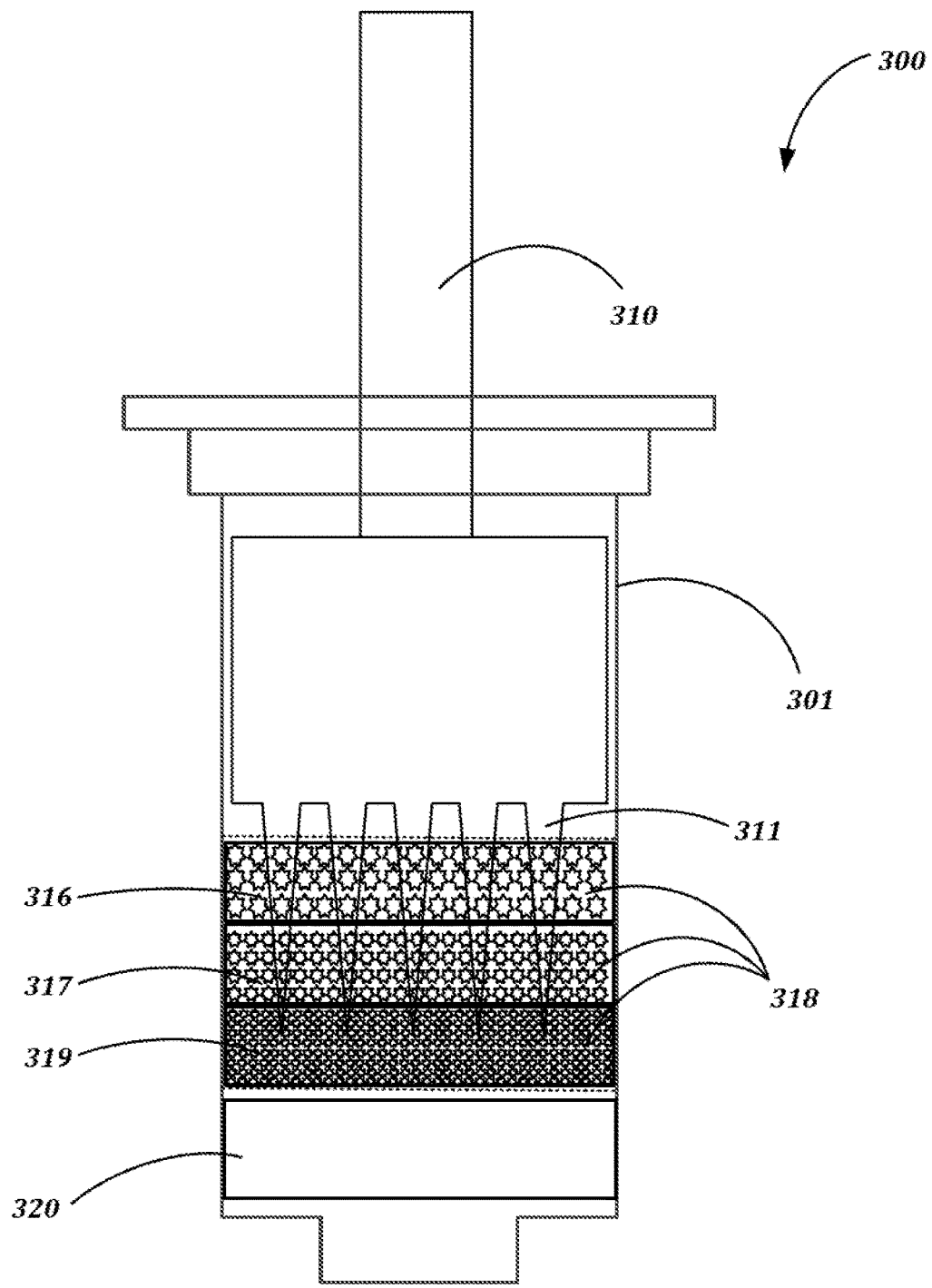
FIG. 9 is a side view of a capture, disruption, and extraction apparatus according to one embodiment.

For example, in an embodiment illustrated in FIGS. 8 and 9, a cell disruption device 300 can include a column 301 having a disruption chamber 304 substantially filled in a similar or the same manner as discussed with respect to other embodiments herein, with a spectrum of abrasive particle layers, for example in one aspect, from large particles 315 to medium particles 317 to small particles 319, from and between opposing portions and/or mesh elements 303, 305, of a portion of disruption chamber 304 toward a middle, intermediate, lower, or central region 307 thereof. The disruption chamber 304 can be fabricated from a tube, column, or any other suitable shape or material.

In one application, the cell sample can be introduced into the disruption chamber 304 according to any of the methods described herein or using a pipette to introduce the sample to a standalone disruption chamber 304, or in a manner as disclosed in U.S. patent application Ser. No. 14/335,946. In one aspect the cells can be induced into the disruption chamber 304 using any suitable biasing mechanism. For example in one embodiment, the apparatus 300 may include a vacuum device to apply a vacuum to the bottom or toward an end or side of the disruption chamber (negative pressure), or a blowing device such as a syringe or pump, to apply positive pressure from the an end or side of the disruption chamber, to induce the sample through the abrasive particles.

In addition, or instead, of the foregoing biasing devices, in some aspects, the apparatus 300 can include a centrifuge device to induce movement of the sample through the abrasives, and trap cells between the abrasive.

In one embodiment as illustrated in FIG. 9, the apparatus 300 includes a pestle 310 including a plurality of agitation members 311. The agitation members 311 can include any suitable disrupting shape or feature, such as conical extrusions such as thorn-like extrusions, at its end. In one aspect, the pestle 310 can be manually and/or automatically actuated to press it into the abrasive layers 315, 317, 319. The apparatus 300 can in one aspect be configured or include a manual and/or automatic actuation device to rotate the pestle 310 and/or the disruption chamber 304 to move or turn the abrasives and cell sample with respect to the agitation members 311, thereby disrupting or breaking the cells to reach its content.

Such an embodiment can combine features of other embodiments, such as routing the cell content through a solid phase extraction matrix to reach a target active agent, and/or including a containment and filtering assembly similar to that described above including a mesh to retain abrasives in the disruption chamber 304.

In some embodiments, the apparatus 300 may include a solid phase extraction matrix 320 positioned downstream the abrasive content 318 and configured to further isolate particular matter or material from the broken cells, such as RNA, DNA, protein, lipids or any combination thereof, and/or any other suitable matter or material desired to be extracted. In some embodiments, the matrix 320 can include a composite or other filtering material such as fiberglass, glass, sand, any combination thereof, and/or any other suitable frit, matrix, and/or binding or filtering material. In one aspect, the matrix 320 can include a Qiagen® RNA extraction membrane.

Figures 10A, 11A:
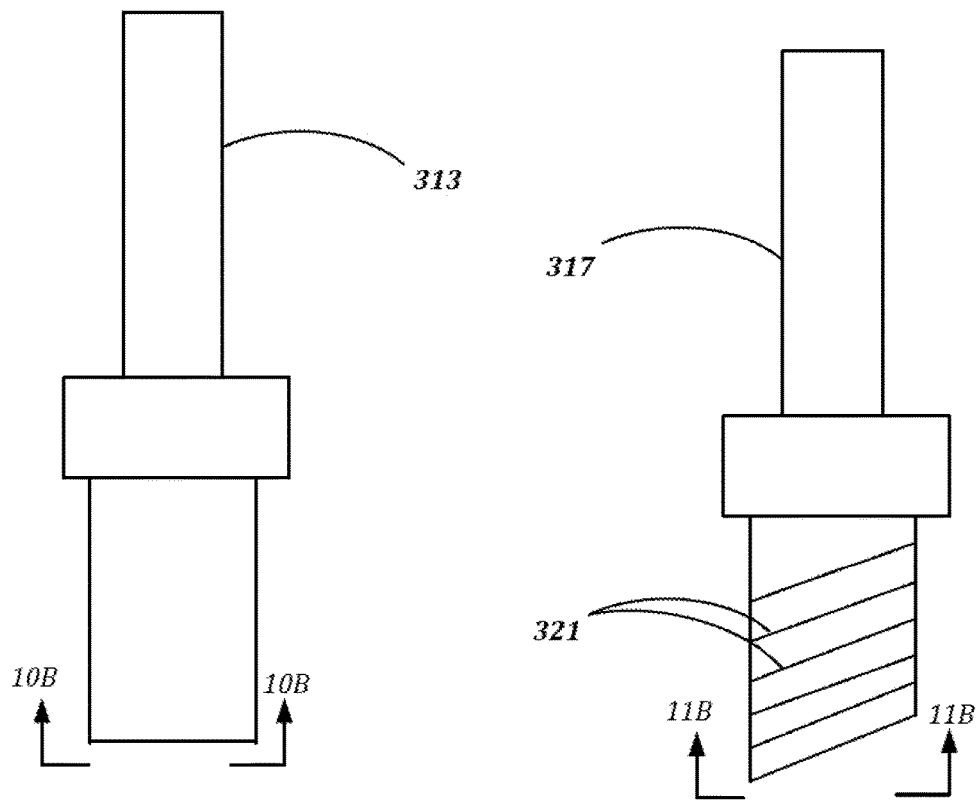
FIGS. 10A and 10B are respectively side and bottom views of a pestle of the apparatus of FIG. 9, according to one embodiment.
FIGS. 11A and 11B are respectively side and bottom views of a pestle of the apparatus of FIG. 9, according to another embodiment.
Figures 10B, 11B:
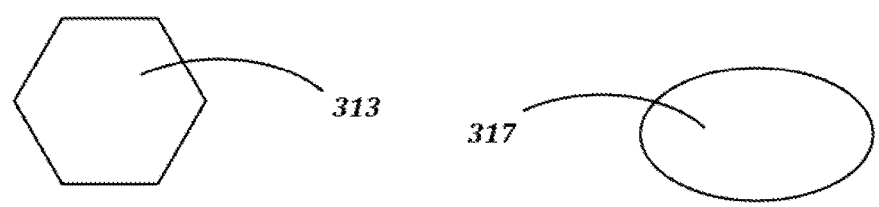

Other pestle arrangements can be incorporated in various embodiments and contemplated to be within the scope of the present disclosure. For example, FIGS. 10A and 10B illustrate a pestle 313 having a hexagonal agitation member 315. Other configurations are possible. For example, FIGS. 11A and 11B illustrate another embodiment including a pestle 317 having an elliptical agitation member 319. Other features can be incorporated in various aspects to bring about additional agitation and/or disruption of cell solution. For example, the agitation member 319 can include ridges or other suitable agitation features 321 on a periphery thereof.

Figures 12, 13, 14:
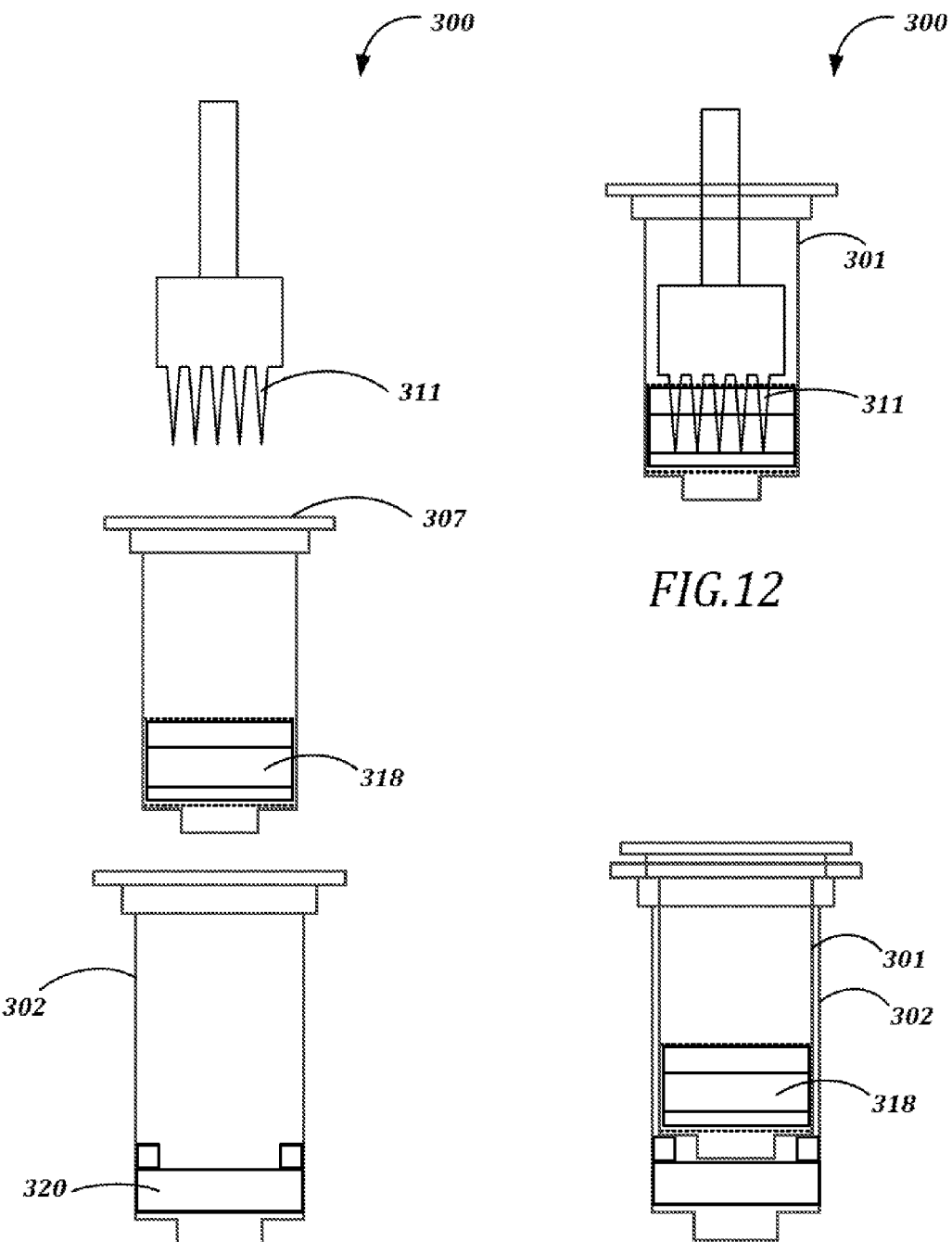
FIG. 12 is a capture, disruption, and extraction apparatus according to one embodiment.
FIG. 13 is a side exploded view of a capture, disruption, and extraction apparatus according to one embodiment.
FIG. 14 is a side view of a portion of the capture, disruption, and extraction apparatus of FIG. 13 according to one aspect.

In yet another aspect as illustrated in FIGS. 12, 13, and 14, the solid phase extraction matrix 320 can be in an outer column 302 in which the column 301 is configured to nest. For example, the column 301 can be in fluid communication with the outer column 302 to communicate thereto, the filtered cell slurry following agitation in the abrasive content 318, to then be further filtered through the matrix 320 positioned downstream in the outer column 302. In one embodiment, the pestle 310 can be operated to disrupt and/or agitate contents of the column 301 in a first step as illustrated in FIG. 12, then the column 301 containing the cell slurry being transferred to couple with the outer column 302 to communicate the slurry thereto and toward the matrix 320 in a second step.

Example

In on example, abrasive particles form a three-dimensional filter in the volume surrounding the pestle inside the disruption chamber, which chamber can be formed from a cylindrical cavity. A fine mesh (e.g., PEEK mesh) is positioned at either end of the disruption chamber to prevent or substantially mitigate the particles from escaping the capture and disruption chamber. For improved cell capture and grinding and/or disruption setup, the setup can in one example be mounted substantially vertically promoting the particles settling into place when loaded. A donut-shaped mesh is positioned on or toward the lower end of the chamber such that the inner hole of the donut fits snugly around the motor shaft, which actuates or rotates the pestle.

A containing and filtering assembly including a screen is positioned adjacent the lower end of the disruption chamber. With the bottom screen in place, which can also be positioned around an axle, the disruption chamber being screwed into, otherwise coupled to, or having an inner hollow portion surrounding the axle. A funnel is placed on top of the chamber to facilitate abrasive particle loading and then the chamber is filled with water using a syringe that is attached to the fluidic inlet of the disruption chamber. After clearing any bubbles in the chamber, the particles settle.

Finally, the abrasive particles, suspended in water or other fluid, are loaded into the chamber with a pipette. The largest particles are loaded first and last, and the smallest particles are loaded as the middle layer. The particles are loaded in discrete volumes (e.g., 30 µl at a time) to enable substantially complete settling and packing. For example, in one embodiment for isolating and grinding cyanobacteria, diamond dust with average particles sizes of 60 µm, 30 µm, and 15 µm is loaded 30 µl at a time. Approximately, 60 µl of 60

μm diamond dust forms the bottom layer, followed by 30 μl of 30 μm diamond dust, 30 μl of 15 μm diamond dust, 30 μl of 30 μm diamond dust, and enough 60 μm diamond dust to fill the rest of the chamber (~60-120 μl).

Sufficient time is allowed between each 30 μl loading for the particles to substantially settle in the chamber. After the initial loading, the syringe at the fluidic inlet of the chamber can be pulled back gently and slowly to help pack the diamond dust, and mitigate or prevent disrupting the layers. The chamber is topped off with 60 μm diamond dust to ensure the chamber is substantially completely full. It is advantageous to substantially fill the chamber because if there is excess space, channels or burrows may form in the diamond dust due to fluid flow; such channels can disrupt the filtration process as the majority of fluid, including cell suspensions, flows through the channel without being filtered.

Once the chamber is substantially full with abrasive particles, the remainder of the water left in the chamber should be pulled out using the syringe. The funnel is removed, a PEEK mesh is placed on top of the chamber to substantially mitigate or prevent particles from spilling out through the outlet port, and the disruption chamber cap is mounted.

Prior to cell loading, the disruption chamber can be washed and primed, for example, with a cell lysis and nuclease-deactivating reagent. After the chamber is washed and primed (if needed), the cell suspension is flowed through the disruption chamber. Flow through the chamber prior to grinding can be maintained at low rates (e.g., 2 μl/min) to substantially not disturb the layers of abrasive particles forming the three dimensional filter.

As the cells are captured in the filter formed by abrasives, the media continues through the device to the outlet where it can be sent to waste. Being three dimensional, the filter is capable of capturing a large number of bacteria as compared to two-dimensional filters. The captured cells can then be exposed to various reagents flowed through the chamber at low rates. In the example of RNA extraction from cyanobacteria, the cells can be exposed to a cell lysis buffer diluted with ethanol. The lysis buffer helps to substantially disrupt the durable cell walls of the bacteria, and the ethanol is included since it promotes the attachment of RNA to the silica gel RNA capture matrix.

Once the cells are ready for grinding, the motor is turned on which activates the stirring mechanism, which may include the pestle coupled to the motor, in the grinding chamber. The stirring mechanism mixes the particles and the bacteria, creating a physical grinding action that disrupts the cells and releases their contents. Diamond dust can be used for grinding because its irregular shape and strength make for many sharp and durable surfaces.

After grinding the cells, any sequence of desired solutions can be flowed over the samples. In the case of RNA extraction from cyanobacteria, a series of wash solutions is flowed through the chamber to first encourage binding of the RNA to the silica capture material and then to clear out non-RNA impurities (e.g., proteins, lipids).

Embodiments of the present disclosure exhibit higher filtration capacity. According to various aspects of the present disclosure, the three-dimensional filter substantially increases the particles trapped at rates faster than other existing filter types, more efficiently and effectively isolating cells.

Embodiments further exhibit higher lysis efficacy, trapping cells between the abrasives, which also lyse them, therefore substantially preventing sample loss and contamination. Furthermore desirable cell lysis parameters can be controlled by selectively controlling the time and rate of rotation of the pestle, and/or via abrasive particle selection and particular distribution from coarse toward opposing ends of the disruption chamber to the central, lower, intermediate, or middle region thereof.

Embodiments of the present disclosure further provide for selective collection of cells or organisms. By using different size particles/abrasives we can selectively determine which size cells can be captured and which can be passed through. Additionally, at least some embodiments are suitable for processing hard to lyse cells. For example, some cells such as plant tissue or bacteria spores are difficult to lyse due to their hard outer shell or cell walls. Abrasives can be selected and used with an embodiment to break any cell type.

Furthermore, embodiments can be formed in an overall small disposable device for sample preparation.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A cell capture, disruption, and extraction apparatus comprising:
   an inlet;
   an outlet;
   a disruption chamber in fluid communication with the inlet and the outlet, the inlet configured to receive cell solution carrying cells and waste matter;
   a pestle at least a portion of which is configured to be received in the disruption chamber;
   a plurality of abrasive particles configured to be positioned in the disruption chamber, the disruption chamber holding the abrasive particles prior to introduction of the cell solution to the disruption chamber, the abrasives being sized and shaped to obstruct cells in a space between the abrasives, and allow therethrough the waste matter following introduction of the cell solution to the disruption chamber; and
   an actuating mechanism operatively coupled to at least one of the disruption chamber and the pestle, and configured to agitate at least one of the pestle and the disruption chamber, the abrasives being sized and shaped to cut the cells separated from the waste matter.

2. The apparatus of claim 1 wherein the abrasive particles are arranged in at least a first layer having a first density of abrasive particles and a second layer having a second density of abrasive particles, the first density being different from the second density.

3. The apparatus in claim 2 wherein the first layer is positioned toward a first end of the disruption chamber and the second layer is positioned toward a second end of the disruption chamber, opposing the first end of the disruption chamber, and the first density is less than the second density.

4. The apparatus of claim 1, further comprising:
an outlet port in fluid communication with the disruption chamber, wherein the abrasives trapping the cells include a material configured to break the cells in response to agitation, forming a slurry, the outlet port configured to communicate fluid from the disruption chamber to an environment away from the disruption chamber.

5. The apparatus of claim 1 wherein the abrasives substantially fill the disruption chamber.

6. The apparatus of claim 1 wherein the abrasive particles each are comprised of an irregular shape.

7. The apparatus of claim 1, further comprising:
a first mesh component configured to be positioned toward a first end of the disruption chamber; and
a second mesh component configured to be positioned toward a second end of the disruption chamber, opposing the first end, the first and second mesh components retaining the abrasives.

8. The apparatus of claim 1 wherein the disruption chamber includes a first column.

9. The apparatus of claim 8, further comprising:
a second column configured to be in fluid communication with the first column, the second column including a binding matrix.

10. An apparatus adapted to trap, filter, grind, and break cells in a fluid having cells and waste matter, the apparatus comprising:
a first fitting forming therein a disruption chamber;
a second fitting coupled to the first fitting and forming an outlet portion therein in fluid communication with the disruption chamber;
an inlet port in fluid communication with the disruption chamber;
a plurality of abrasives positioned in the disruption chamber prior to introduction of fluid to the disruption chamber, forming a multi-dimensional filtration and grinding tool, the plurality of abrasives being arranged in a plurality of layers, each layer having distinct densities, at least one of the layers having abrasives sized and shaped to allow therethrough the waste matter, and obstruct in a space between the abrasives the cells; and
an actuation device operatively coupled to a pestle engaging the disruption chamber and configured to rotate therewith, agitating the disruption chamber, the abrasives in the at least one of the layers being comprised of a material and shape to cut the cells, separated from waste matter, in response to agitation.

11. The apparatus of claim 10, further comprising:
at least one retaining member including a mesh component, the at least one retaining member positioned adjacent at least one of the inlet and outlet of the disruption chamber.

12. A cell disruption chamber comprising:
a disruption volume having an inlet and an outlet and configured to receive a cell solution containing cells;
a plurality of abrasive particles configured to be positioned in the disruption volume prior to introduction of the cell solution to the disruption volume, the abrasives sized and shaped to obstruct the cells in a space between the abrasives, thereby filtering the cells from the cell solution and allowing therethrough waste matter from cell solution;
an actuation device configured to agitate the disruption volume, the abrasives being sized and shaped to cut the cells separated from the waste matter, the actuation device operatively coupled to the disruption volume wherein the actuation device includes a pestle configured to at least one of move, agitate, rotate, and shake the disruption volume, grinding the abrasives against the cells;
an inlet in fluid communication with the disruption volume; and
an outlet in fluid communication with the disruption volume.

13. The disruption chamber of claim 12 wherein the plurality of abrasives are arranged in at least a first layer and a second layer, the abrasives of the first layer being larger than the abrasives in the second layer, the first layer guiding the cell solution toward the second layer, and the second layer trapping the cells and allowing the waste matter therethrough.

* * * * *